United States Patent
Liao et al.

(10) Patent No.: US 9,776,955 B2
(45) Date of Patent: Oct. 3, 2017

(54) METHOD FOR PREPARING N,N'-BIS(2-CYANOETHYL)-1,2-ETHYLENEDIAMINE

(71) Applicant: NAN YA PLASTICS CORPORATION, Taipei (TW)

(72) Inventors: Te-Chao Liao, Taipei (TW); Jung-Jen Chuang, Taipei (TW); Zhi-Ming Huang, Taipei (TW); Shun-Chi Chen, Taipei (TW); Tzu-Chiang Lin, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 15/355,103

(22) Filed: Nov. 18, 2016

(65) Prior Publication Data

US 2017/0152215 A1    Jun. 1, 2017

(30) Foreign Application Priority Data

Nov. 26, 2015   (TW) .............................. 104139367 A

(51) Int. Cl.
*C07C 253/18* (2006.01)

(52) U.S. Cl.
CPC .................................. *C07C 253/18* (2013.01)

(58) Field of Classification Search
None
See application file for complete search history.

(56) References Cited

U.S. PATENT DOCUMENTS

2008/0194857 A1* 8/2008 Hayes ................... C07C 209/48
558/452

* cited by examiner

*Primary Examiner* — Samantha Shterengarts
(74) *Attorney, Agent, or Firm* — Bacon & Thomas, PLLC

(57) ABSTRACT

A method for preparing N,N'-bis(2-cyanoethyl-1,2-ethylenediamine involves using glycol ether as a catalyst for synthesis reaction in which ethylenediamine and acrylonitrile at a molar ratio of 1:1.9-2.1 are reactant that react at 20-70°C to prepare N,N'-bis(2-cyanoethyl)-1,2-ethylenediamine; the method improves the yield to 98.15-98.98%; and the used glycol ether may be filtered and recycled, thereby saving costs and reducing environmental pollution.

7 Claims, No Drawings

METHOD FOR PREPARING N,N'-BIS(2-CYANOETHYL)-1,2-ETHYLENEDIAMINE

BACKGROUND OF THE INVENTION

1. Field of the Invention

The present invention relates to N,N'-bis(2-cyanoethyl)-1,2-ethylenediamine (hereinafter shortened as BCNEDA), and more particularly to a method for preparing BCNEDA with an improved yield.

2. Description of Related Art

Conventionally, synthesis of BCNEDA uses acetic acid, water, monol-based solvent (e.g., ethanol, isopropanol or methanol) or other promoters as a catalyst for promoting reaction. However, acetic acid can corrode the equipment and other solvents are not helpful to enhance the yield of BCNEDA so there is a need of distillation for product purification.

For example, DE 2446489A1 has in 1976 disclosed a process in which acrylonitrile and ethylenediamine at a molar ratio of 2:1 are used. Acrylonitrile containing therein acetic acid as a catalyst is added into ethylenediamine (EDA) within 2 hours. According to this disclosed process, the obtained product after distillation can give BCNEDA at a yield of 98.1%. Nevertheless, acetic acid used in the process can corrode the equipment and this prevented the process from commercial applications.

As another example, US 2008/0194857A1 discloses a method wherein water is used as a solvent and then acrylonitrile and ethylenediamine at a molar ratio of 2:1 react in the presence of 2-30 wt % of water based on the total reactants to synthesize N,N'-bis(2-cyanoethyl)-1,2-ethylenediamine When the amount of water is 20 wt %, the yield of BCNEDA reaches 93.78%.

Additionally, it is known in the art to use a monol-based solvent (e.g., ethanol, isopropanol or methanol) as a catalyst and to have acrylonitrile and ethylenediamine at a molar ratio of about 2:1 react in the presence of 60-120 wt % of a monol-based solvent based on total reactant, thereby synthesizing BCNEDA. The ethanol solvent provides the most preferred result for it gives a yield of BCNEDA as high as 97.60%.

SUMMARY OF THE PRESENT INVENTION

The present invention discloses a method for preparing BCNEDA, which involves: adding 10-51.04 wt % of a glycol ether in a reactor (e.g. a three-neck round-bottom flask) based on the total weight of the reactant; stirring and adding ethylenediamine to homogeneity; at room temperature, adding dropwise acrylonitrile in an amount that a molar ratio between ethylenediamine and acrylonitrile is 1:1.9-2.1 within 2 hours and under 70° C.; proceeding with the reaction at 25-70° C., preferably 30-65° C.; using gas chromatography (GC) to verify that conversion of ethylenediamine reaches 100% and finishing the reaction if so. Analysis of the product of the reaction confirms that the yield of BCNEDA is as high as 98.15-98.98%.

The glycol ether may be filtered and recycled, and is one selected from the group consisting of ethylene glycol monomethyl ether (EM), di-ethylene glycol monomethyl ether (DEM), triethylene glycol monomethyl ether (TEM), ethylene glycol monoethyl ether (EE), di-ethylene glycol monoethyl ether (DE), poly-ethylene glycol monoethyl ether (PEE), ethylene glycol monobutyl ether (EB), di-ethylene glycol monobutyl ether (DEB), triethylene glycol monobutyl ether (TEB), poly-ethylene glycol monobutyl ether (PEB), ethylene glycol propyl ether(EP), di-ethylene glycol propyl ether (DEP), proprylene glycol monomethyl ether (PM), di-proprylene glycol monomethyl ether (DPM), propylene glycol monoehtyl ether (PE), di-propylene glycol monoehtyl ether (DPE), propylene glycol monobutyl ether (PNB), di-propylene glycol monobutyl ether (DPNB), propylene glycol propyl ether (PP) and di-propylene glycol propyl ether (DPP).

The method for preparing BCNEDA according to the present invention has the following advantages:
1. By using a glycol ether as the catalyst for the synthesis reaction, the yield of BCNEDA is improved to higher than 98.0%;
2. by using a glycol ether as the catalyst instead of acetic acid, water and monol-based solvent for the synthesis reaction, the present invention breaks the stereotype that BCNEDA is conventionally made using acetic acid, water or monol-based solvent as a solvent; and
3. the glycol ether that has been used in the method may be filtered and recycled, thereby saving costs and reducing environmental pollution.

DETAILED DESCRIPTION OF THE INVENTION

The method for preparing BCNEDA according to the present invention takes ethylenediamine and acrylonitrile with a certain ratio as the reactant to perform a synthesis reaction in the presence of a glycol ether. The final reactant after the reaction improve the yield of BCNEDA to 98.15-98.98%.

The disclosed method for preparing BCNEDA comprising the following steps:
a) in a reactor (such as a three-neck round-bottom flask), adding a glycol ether in an amount of 10-51.04 wt % based on a total weight of the reactants, preferably 30-51.04 wt % nd more preferably 47 wt %;
b) adding ethylenediamine into the glycol ether solution of step a) and stirring to homogeneity;
c) at a temperature of 25-70° C., preferably 30-65° C., adding dropwise acrylonitrile in an amount that a molar ratio between ethylenediamine and acrylonitrile is 1:1.9-2.1 (preferably 1:2.0) under a temperature below 70° C. because acrylonitrile tends to have self-polymerization at a temperature higher than 70° C.;
d) performing the reaction at a temperature of 25-70° C., preferably 30-65° C., for 2.5-25 hours, using gas chromatography (GC) to verify that conversion of ethylenediamine reaches 100% and finishing the reaction if so. Analysis of the product of the reaction confirms that the yield of BCNEDA is 98.0% or more.

In the disclosed method for preparing BCNEDA, by introducing acrylonitrile in the following alternative ways, the yield of BCNEDA can also achieve 98.0% or more:
1. adding ethylenediamine and acrylonitrile simultaneously and continuously into the reactor;
2. mixing ethylenediamine and the glycol ether first and then adding them together into the reactor; or
3. adding acrylonitrile continuously into the reactor.

The critical technique of the present invention is to use a glycol ether as the catalyst for the synthesis reaction, to improve the yield of BCNEDA to 98.15-98.98% or more. The process is simple and safe. In addition, the used glycol ether may be filtered and recycled, thereby saving costs and reducing environmental pollution.

The glycol ether is one selected from the group consisting of ethylene glycol monomethyl ether (EM), di-ethylene glycol monomethyl ether (DEM), triethylene glycol monomethyl ether (TEM), ethylene glycol monoethyl ether (EE), di-ethylene glycol monoethyl ether (DE), poly-ethylene glycol monoethyl ether (PEE), ethylene glycol monobutyl ether (EB), di-ethylene glycol monobutyl ether (DEB), triethylene glycol monobutyl ether (TEB), poly-ethylene glycol monobutyl ether (PEB), ethylene glycol propyl ether (EP), di-ethylene glycol propyl ether(DEP), proprylene glycol monomethyl ether (PM), di-proprylene glycol monomethyl ether (DPM), propylene glycol monoehtyl ether (PE), di-propylene glycol monoehtyl ether (DPE), propylene glycol monobutyl ether (PNB), di-propylene glycol monobutyl ether (DPNB), propylene glycol propyl ether (PP) and di-propylene glycol propyl ether (DPP). And, the glycol ether is preferably proprylene glycol monomethyl ether (PM).

While the following examples are herein discussed for further explaining the present invention, the scope of the present invention is not limited thereto.

EXAMPLE 1

In a 250 mL three-neck flask equipped with a condenser and a mechanical agitator, 12.002 g (0.2 mol) of ethylenediamine (hereinafter shortened as EDA) and 30.000 g of propylene glycol monomethyl ether (PM) were added. Then 21.827 g (0.411mol) of acrylonitrile (hereinafter shortened as ACN) was added dropwise at room temperature in a process shorter than 2 hours. Throughout the process, the temperature was controlled below 70° C.

After dropwise addition of ACN was completed, the reactant were left for reaction for 24 hours at 25° C. At the end of the reaction, gas chromatography (hereinafter shortened as GC) was used to confirm that conversion of EDA reached 100%.

After the reaction, a final reaction product was obtained and further analyzed in terms of composition, and the results are shown in Table 1.

The yield of BCNEDA is 98.98%.

EXAMPLE 2

In a 250 mL three-neck flask equipped with a condenser and a mechanical agitator, 12.002 g (0.2 mol) of EDA and 30.000 g of PM were added. At 60° C., 21.827 g (0.411 mol) of ACN was added dropwise within a time period shorter than 2 hours with the temperature held below 70° C.

After ACN was added dropwise, the reaction took place continuously for 2.5 hours at 65° C. GC was used to verify that conversion of EDA reached 100%.

After the reaction, a final reaction product was obtained and further analyzed in terms of composition, and the results are shown in Table 1.

The yield of BCNEDA is 98.46%.

EXAMPLE 3

The process was similar to that of Example 2, but PM used was 3.76 g instead of 30.0 g. After the reaction, a final reaction product was obtained and further analyzed in terms of composition, and the results are shown in Table 1.

The yield of BCNEDA is 98.15%.

EXAMPLE 4

The process was similar to that of Example 2, but PM used was 32.14 g instead of 30.0 g. After the reaction, a final reaction product was obtained and further analyzed in terms of composition, and the results are shown in Table 1.

The yield of BCNEDA is 98.55%.

EXAMPLE 5

The process was similar to that of Example 2, but ACN used was 21.191 g (0.400 mol) instead of 21.827 g (0.411 mol). After the reaction, a final reaction product was obtained and further analyzed in terms of composition, and the results are shown in Table 1.

The yield of BCNEDA is 98.55%.

EXAMPLE 6

The process was similar to that of Example 2, but PM used was 14.5 g instead of 30.0 g. After the reaction, a final reaction product was obtained and further analyzed in terms of composition, and the results are shown in Table 1.

The yield of BCNEDA is 98.45%.

COMPARATIVE EXAMPLE 1

In a 1000 mL three-neck flask, 120.000 g (2.0 mol) of EDA and 300.000 g of methanol solution were added. At room temperature, 217.000 g (4.1 mol) of ACN was added dropwise within a time period shorter than 2 hours with the temperature held below 60° C.

After ACN was added dropwise, the reaction took place continuously for 2 hours at 60° C. GC was used to verify that conversion of EDA reached 100%.

After the reaction, a final reaction product was obtained and further analyzed in terms of composition, and the results are shown in Table 1.

The yield of BCNEDA is 90.00%.

COMPARATIVE EXAMPLE 2

The process was similar to that of Comparative Example 1 but ethanol was used instead of methanol and ACN used was 213.0 g instead of 217.0 g.

After the reaction, a final reaction product was obtained and further analyzed in terms of composition, and the results are shown in Table 1.

The yield of BCNEDA is 97.60%.

COMPARATIVE EXAMPLE 3

The process was similar to that of Comparative Example 1 but isopropanol was used instead of methanol.

After the reaction, a final reaction product was obtained and further analyzed in terms of composition, and the results are shown in Table 1.

The yield of BCNEDA is 89.00%.

COMPARATIVE EXAMPLE 4

In a 100 mL three-neck flask equipped with a condenser and a mechanical agitator, 14.7 g (0.244 mol) of EDA and 10.2 g of water were added. The mixture was sparged with nitrogen gas for 30 minutes.

Then the agitator is turned on and the mixture was heated to 50° C. 25.9 g (0.488 mol) of ACN was added dropwise within 2 hours. Afterward, the mixture was cooled to room temperature. GC was used to verify that conversion of EDA reached 100%.

After the reaction, a final reaction product was obtained and further analyzed in terms of composition, and the results are shown in Table 1.

The yield of BCNEDA is 93.78%.

TABLE 1

| Components (wt %) | Examples | | | | | | Comparative Examples | | | |
|---|---|---|---|---|---|---|---|---|---|---|
| | 1 | 2 | 3 | 4 | 5 | 6 | 1 | 2 | 3 | 4 |
| EDA[1] (g) | 12.002 | 12.002 | 12.002 | 12.002 | 12.002 | 12.002 | 120.00 | 120.00 | 120.00 | 14.700 |
| ACN[2] (g) | 21.827 | 21.827 | 21.827 | 21.827 | 21.191 | 21.827 | 217 | 213 | 217 | 25.9 |
| EDA/ACN Molar ratio | 1/2.06 | 1/2.06 | 1/2.06 | 1/2.06 | 1/2.00 | 1/2.06 | 1/2.05 | 1/2.01 | 1/2.05 | 1/2.00 |
| PM[3] (g) | 30.0 | 30.0 | 3.76 | 32.14 | 30.0 | 14.5 | — | — | — | — |
| Methanol (g) | — | — | — | — | — | — | 300.0 | — | — | — |
| Ethanol (g) | — | — | — | — | — | — | — | 300.0 | — | — |
| Isopropanol (g) | — | — | — | — | — | — | — | — | 300.0 | — |
| Water (g) | — | — | — | — | — | — | — | — | — | 10.2 |
| ACN's Dropwise Adding Temperature | 25° C. | 60° C. | 60° C. | 60° C. | 60° C. | 60° C. | 60° C. | 60° C. | 60° C. | 50° C. |
| Ratio between PM and the total weight of the reactants[4] (%) | 47.0 | 47.0 | 10.0 | 51.04 | 47.47 | 30.0 | — | — | — | — |
| Reaction Temperature | 25° C. | 65° C. | 65° C. | 65° C. | 65° C. | 65° C. | 60° C. | 60° C. | 60° C. | — |
| Reaction Duration (hours) | 24 | 2.5 | 2.5 | 2.5 | 2.5 | 2.5 | 2.0 | 2.0 | 2.0 | — |
| BCNEDA's Yield[5] (%) | 98.98 | 98.46 | 98.15 | 98.55 | 98.55 | 98.45 | 90.00 | 97.60 | 89.00 | 93.7 |

Note:
1. Ethylenediamine, produced by Tedia Company, Inc.;
2. Acrylonitrile, produced by Hayashi Pure Chemical Ind., Ltd.;
3. Proprylene glycol monomethyl ether, reagent-grade, produced by Acros Organics;
4. The total reactant weight refers to the sum of the weights of glycol ether, ethylenediamine and acrylonitrile.
5. Yield (%) = Conversion (%) × Selectivity (%)

CONCLUSION

1. As demonstrated in Examples 1-6 and Comparative Examples 1-4, for preparing BCNEDA, it is possible to use a glycol ether instead of acetic acid, water or monol-based solvent as a catalyst for synthesis.
2. As demonstrated in Examples 1-6 and Comparative Examples 1-4, for preparing BCNEDA, by making ethylenediamine and acrylonitrile with a certain ration perform synthesis reaction in the presence of a glycol ether solution, the yield of BCNEDA can be improved to as high as 98.15-98.98%, superior to the conventional method where synthesis reaction of N,N'-bis(2-cyanoethyl)-1,2ethylenediamine is performed in the presence of acetic acid, water or monol-based solvent.
3. In Examples 1-2 and 4-6, the yield of BCNEDA is even higher, of which yield is up to 98.45-98.98%. The amount of the glycol ether used is 30-51.04 wt % of the total weight of the reactants.

What is claimed is:

1. A method for preparing N,N'-bis(2-cyanoethyl)-1,2-ethylenediamine, comprising
   a) taking ethylenediamine and acrylonitrile at a molar ratio therebetween of 1:1.9-2.1 as reactants;
   b) performing a synthesis reaction in the presence of a glycol ether at a reaction temperature of 25-70° C. until conversion of ethylenediamine reaches 100%; and
   c) after the reaction is completed, N,N'-bis(2-cyanoethyl)-1,2-ethylenediamine is produced at a yield of 98.15-98.98%;
   wherein the glycol ether is added in an amount of 10-51.04 wt % based on a total weight of the reactants, and
   wherein the glycol ether is one selected from the group consisting of ethylene glycol monomethyl ether (EM), di-ethylene glycol monomethyl ether (DEM), triethylene glycol monomethyl ether (TEM), ethylene glycol monoethyl ether (EE), di-ethylene glycol monoethyl ether (DE), poly-ethylene glycol monoethyl ether (PEE), ethylene glycol monobutyl ether (EB), di-ethylene glycol monobutyl ether (DEB), triethylene glycol monobutyl ether (TEB), poly-ethylene glycol monobutyl ether (PEB), ethylene glycol propyl ether(EP), di-ethylene glycol propyl ether(DEP), propylene glycol monomethyl ether (PM), di-propylene glycol monomethyl ether (DPM), propylene glycol monoethyl ether (PE), di-propylene glycol monoethyl ether (DPE), propylene glycol monobutyl ether (PNB), di-propylene glycol monobutyl ether (DPNB), propylene glycol propyl ether (PP) and di-propylene glycol propyl ether (DPP).

2. The method of claim 1, wherein glycol ether is added in an amount of 30-51.04 wt % based on the total weight of the reactant.

3. The method of claim 1, wherein glycol ether is added in an amount of 47 wt % based on the total weight of the reactant.

4. The method of claim 1, wherein the molar ratio between ethylenediamine and acrylonitrile is 1:2.06.

5. The method of claim 1, wherein the molar ratio between ethylenediamine and acrylonitrile is 1:2.0.

6. The method of claim 1, wherein acrylonitrile is added dropwise to react with ethylenediamine.

7. The method of claim 1, wherein the synthesis reaction in the presence of the glycol ether is performed at the reaction temperature of 30-65° C.

* * * * *